United States Patent [19]

Hossain et al.

[11] Patent Number: 5,611,808
[45] Date of Patent: Mar. 18, 1997

[54] BLADE ASSEMBLY RECEPTACLE AND METHOD

[75] Inventors: K. Mosaddeq Hossain, Somerville, N.J.; Krzysztof Gacek, Philadelphia, Pa.

[73] Assignee: Cabot Technology Corporation, Wilmington, Del.

[21] Appl. No.: 527,228

[22] Filed: Sep. 12, 1995

[51] Int. Cl.⁶ .................................................. A61B 17/32
[52] U.S. Cl. ........................ 606/170; 606/167; 81/121.1
[58] Field of Search .................................... 606/120, 170, 606/142, 167, 169; 227/180; 81/121.1, 124.3, 472, 476, 478

[56] References Cited

U.S. PATENT DOCUMENTS

| | | |
|---|---|---|
| 3,934,715 | 1/1976 | Antonini et al. . |
| 4,106,620 | 8/1978 | Brimmer . |
| 4,157,758 | 6/1979 | Kozlowski, Jr. . |
| 4,170,234 | 10/1979 | Graham . |
| 4,985,034 | 1/1991 | Lipton ..................................... 606/167 |
| 4,997,084 | 3/1991 | Opie et al. . |
| 5,059,210 | 10/1991 | Clark et al. ............................. 606/167 |
| 5,163,553 | 11/1992 | Cantwell et al. . |
| 5,342,380 | 8/1994 | Hood . |

OTHER PUBLICATIONS

"*Uniquely* Tripolar™" Brochure.
"Laparoscopic technology now available for open procedures." Brochure.
"A must-have product for advanced laparoscopic surgery." Brochure.

*Primary Examiner*—Michael Powell Buiz
*Assistant Examiner*—Kevin Truong
*Attorney, Agent, or Firm*—Austin R. Miller

[57] ABSTRACT

A receptacle is provided for a removable and replaceable tool of a reusable device. The receptacle has a receptacle body shaped to accommodate a portion of the tool. A passageway is provided at one end of the receptacle body and a receiving member is provided at the other end of the receptacle body. The receiving member is mounted for reciprocal movement with respect to the receptacle body. An exterior end portion of the receiving member is positioned outside the receptacle body for manipulation of the receiving member. An internal end portion is positioned within the receptacle body and is shaped to engage a portion of the tool. Also provided is a method for removing a removable and replaceable tool from a reusable device.

18 Claims, 13 Drawing Sheets

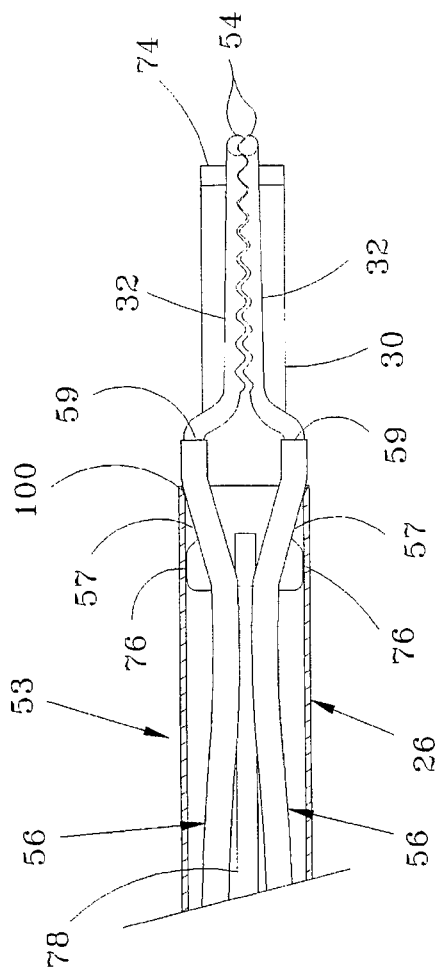
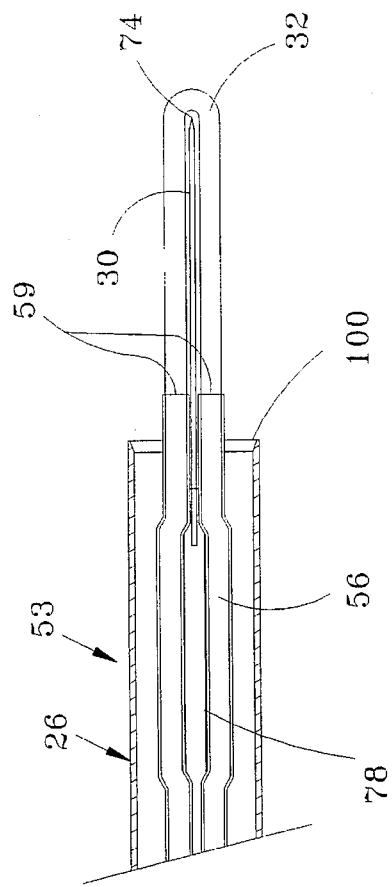
Fig. 2A
Fig. 2B

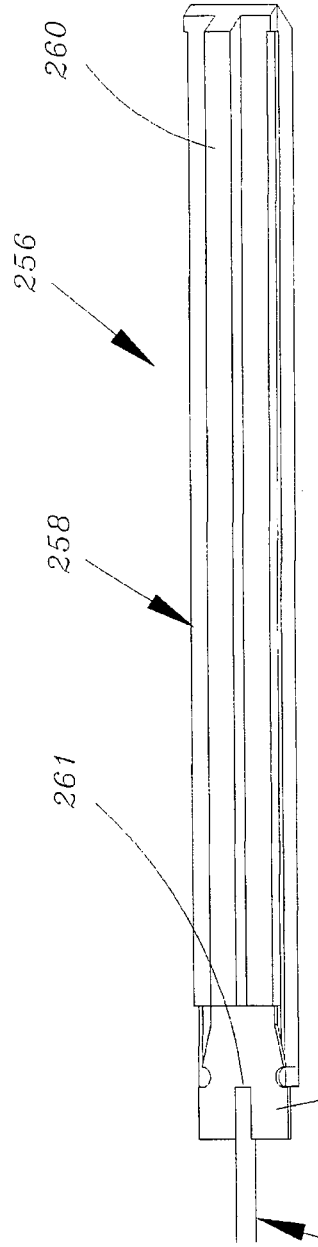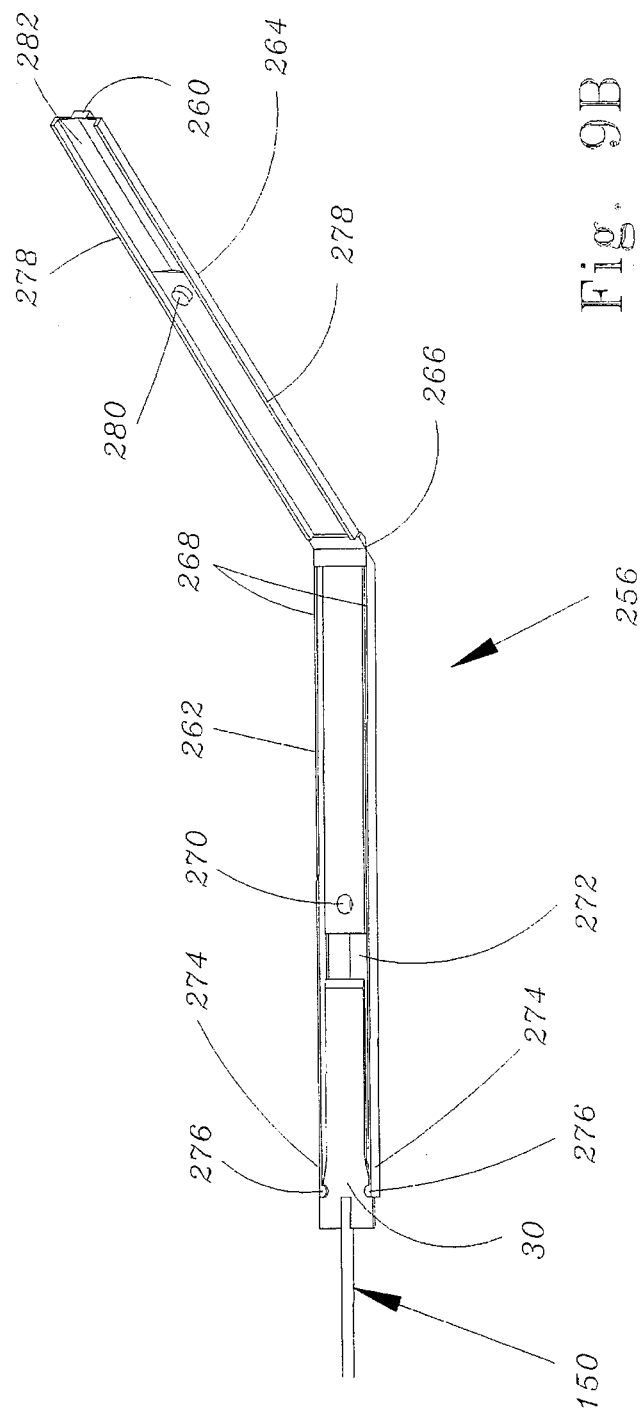

5,611,808

BLADE ASSEMBLY RECEPTACLE AND METHOD

BACKGROUND OF THE INVENTION

This invention relates to a receptacle adapted to contain a tool to permit safe handling of the tool. A preferred embodiment of this invention relates to a receptacle for removing and replacing a blade assembly releasably mounted in a reusable surgical device adapted for gripping, cauterizing and cutting tissue during a surgical procedure.

FIELD OF THE INVENTION

The development of minimally invasive surgical procedures (such as endoscopic and laparoscopic procedures, for example) has created a great demand for surgical devices well adapted for use during such procedures. For example, there is a great demand for a device capable of cutting tissue while preventing excessive bleeding.

An improved surgical device is described in co-pending U.S. patent application Ser. No. 08/160,213 now U.S. Pat. No. 5,458,598 filed Dec. 2, 1993, and is embodied in the SEITZINGER TRIPOLARC™ Cutting Forceps available from Cabot Medical Corporation, 2150 Cabot Boulevard West, Langhorne, Pa. 19047. The SEITZINGER TRIPOLAR™ forceps device has a mechanical cutting blade and bipolar coagulating jaws. The bipolar jaws grasp tissue to be severed and a high-frequency voltage is applied across the jaws to coagulate the tissue. Once coagulated, the tissue is mechanically cut by advancing the blade.

The SEITZINGER TRIPOLAR™ forceps device is disposable. A new device is used for each surgical procedure to provide a clean and sharp blade. The used device is then discarded. Such a disposable device is highly desirable. Disposable surgical devices are frequently inexpensive to purchase because they need not be designed to withstand multiple uses and multiple sterilizations. However, there remains a need for surgical devices that are reusable for multiple procedures to reduce the cost of the device per procedure.

Providing a reusable device presents unique challenges. It may be necessary for the device to have a tool that is removable and replaceable periodically or between surgical procedures. For example, the blade of the SEITZINGER TRIPOLAR™ forceps device could be damaged during or between surgical procedures. On the other hand, a removable and replaceable blade is preferably contained during removal and replacement to reduce the risk of injury or infection of the operator of the surgical device or one who handles the removed blade.

Accordingly, there remains a demand for a receptacle for a removable tool of a reusable device to permit safe and efficient removal and replacement of the tool.

SUMMARY OF THE INVENTION

It is an object of this invention to provide a receptacle for a removable tool of a reusable device to permit safe and efficient removal or replacement of the tool. Another object of this invention is to provide a method for safe and easy removal or replacement of a removable and replaceable tool. Other objects will become clear to those of skill in this art in view of the following disclosure.

This invention provides a receptacle having a body shaped to receive an operative end of a removable and replaceable tool. The receptacle body has a passageway at one end for receiving the operative end of the tool. A receiving member or plunger is provided at an opposite end of the receptacle body for reciprocal movement. The plunger has a portion that is accessible from outside the receptacle body and a tool grasping means positioned within the receptacle body to grasp the tool.

This invention also provides a method for removing or replacing the tool by placing the receptacle body over the operative end of the tool and by grasping the operative end of the tool with the plunger. The receptacle body is then removed from the reusable device together with the tool for disposal. The receptacle is optionally provided with a replacement tool for insertion of the replacement tool into the reusable device.

BRIEF DESCRIPTION OF THE DRAWINGS

FIG. 2A is a cross-sectional side view of a portion of the surgical device shown in FIG. 2 in a blade-advanced and jaws-closed position.

FIG. 2B is a cross-sectional top view of the portion of the surgical device shown in FIG. 2A.

FIG. 9A is a perspective view of an embodiment of a component of the blade assembly receptacle illustrated in FIG. 8, shown with a blade assembly captured therein.

FIG. 9B is a perspective view of the component illustrated in FIG. 9A, shown with a cover portion open and with a blade assembly mounted therein.

DETAILED DESCRIPTION OF THE INVENTION

Figure 1:
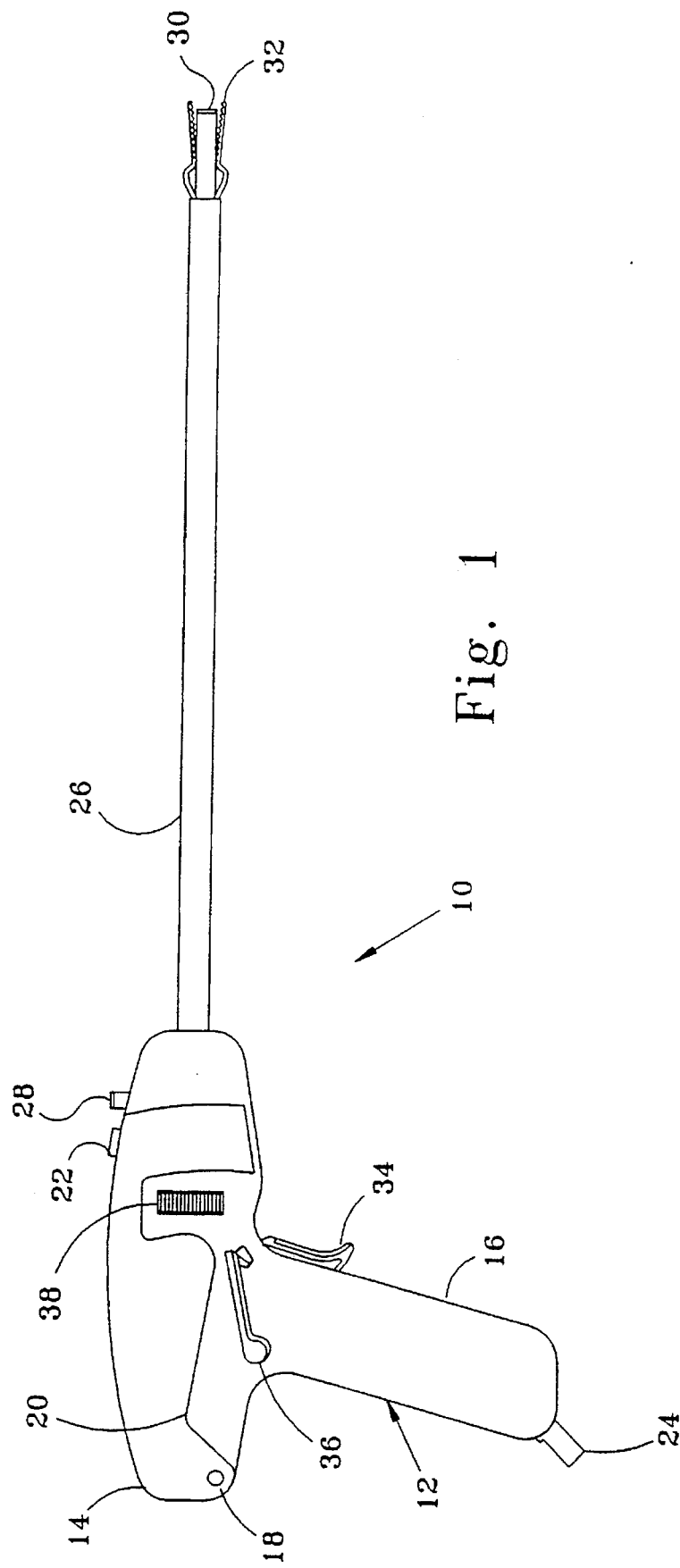
FIG. 1 is a side view of a reusable surgical device adapted for use with the receptacle and method of this invention.

The following description is intended to refer to the specific embodiments of the invention illustrated in the drawings. This description is not intended to define or limit the scope of the invention, which is defined separately in the claims that follow.

Referring to FIG. 1, the numeral "10" generally designates one possible embodiment of a reusable surgical device adapted for use with the blade assembly receptacle of this invention. Surgical device 10 is adapted for use during electrosurgical procedures wherein tissue is grasped and electrical energy is applied to the grasped tissue for cauterization or coagulation. Cauterized or coagulated tissue is then cut mechanically by the device. In other words, surgical device 10 is suited for cutting tissue while preventing excessive bleeding. Surgical device 10 is specifically adapted for laparoscopic, endoscopic or similar procedures wherein the operative portions of surgical devices are introduced into an operative area through a cannula or other port formed in the patient.

Surgical device 10 is reusable for multiple operations. Surgical device 10 is adapted for sterilization between such procedures with commonly used sterilization techniques. However, at least one tissue contacting tool of surgical device 10 is removable for replacement periodically or between surgical procedures. Surgical device 10 is suitable for use with a receptacle according to this invention that is adapted to permit safe and easy removal of a used tool and replacement with a new tool.

Surgical device 10 has a handle 12 for manipulating the device. Handle 12 is provided with a handle cover 14 and a handle body 16. Handle cover 14 is movable relative to handle body 16 between opened and closed positions by means of a cover hinge 18. Handle cover 14 and handle body 16 contact one another along a contact line 20 when handle cover 14 is in a closed position. Contact line 20 extends from a location near cover hinge 18 and to a location near a cover lock 22. Cover lock 22 is positioned to lock handle cover 14 in a closed position with respect to handle body 16.

A bipolar plug 24 is provided at a bottom portion of handle body 16. Bipolar plug 24 provides access for the electrical potential necessary to coagulate and cauterize tissue, as will be described below. Such bipolar plugs are well known.

Handle cover 14 and handle body 16 of handle 12 are preferably molded from a plastic material that is capable of withstanding the conditions of repeated sterilizations. Most preferably, handle cover 14 and handle body 16 are molded from PES or PPS engineering plastic such as RADEL, available from Amoco Chemicals. Also, handle cover 14 and handle body 16 each preferably comprises two side components which are mirror images of one another. In other words, two complimentary halves preferably form handle cover 14 and two complimentary halves preferably form handle body 16.

Surgical device 10 also has an elongated sheath 26 which is connected to handle 12. A female luer lock 28 is connected to elongated sheath 26 for the introduction of cleaning fluid and gases during sterilization of surgical device 10 between surgical procedures. Female luer lock 28, which acts as a cleaning port, extends from an upper portion of handle body 16 and communicates with an interior of elongated sheath 26.

Surgical device 10 also has a removable and replaceable tissue contacting tool, in this embodiment a blade assembly including a blade 30, shown in a fully advanced position in FIG. 1. Extending from elongated sheath 26 of surgical device 10 is a tissue manipulator which, in this embodiment, takes the form of opposed jaws 32 shown in an opened position.

A jaw actuation trigger 34 is provided on handle body 16 of handle 12 to open and close opposed jaws 32 by depressing and releasing trigger 34, respectively. An external blade actuation lever 36 is also provided on handle body 16 of handle 12 to advance or retract blade 30. Surgical device 10 also includes a jaw and blade rotation wheel 38 on handle body 16. Rotation wheel 38 permits an operator of surgical device 10 to rotate the jaw and blade during a surgical procedure to orient the blade and jaws to grasp, cauterize and cut tissues that are positioned in a variety of orientations with respect to handle 12.

As will be described, surgical device 10 is reusable for multiple surgical procedures and is suitable for use with a receptacle adapted to permit safe and easy removal of blade 30 so that a clean and sharp cutting edge can be safely and easily installed for each surgical procedure. The remaining components of surgical device 10 are sterilized between surgical procedures.

Figure 2:
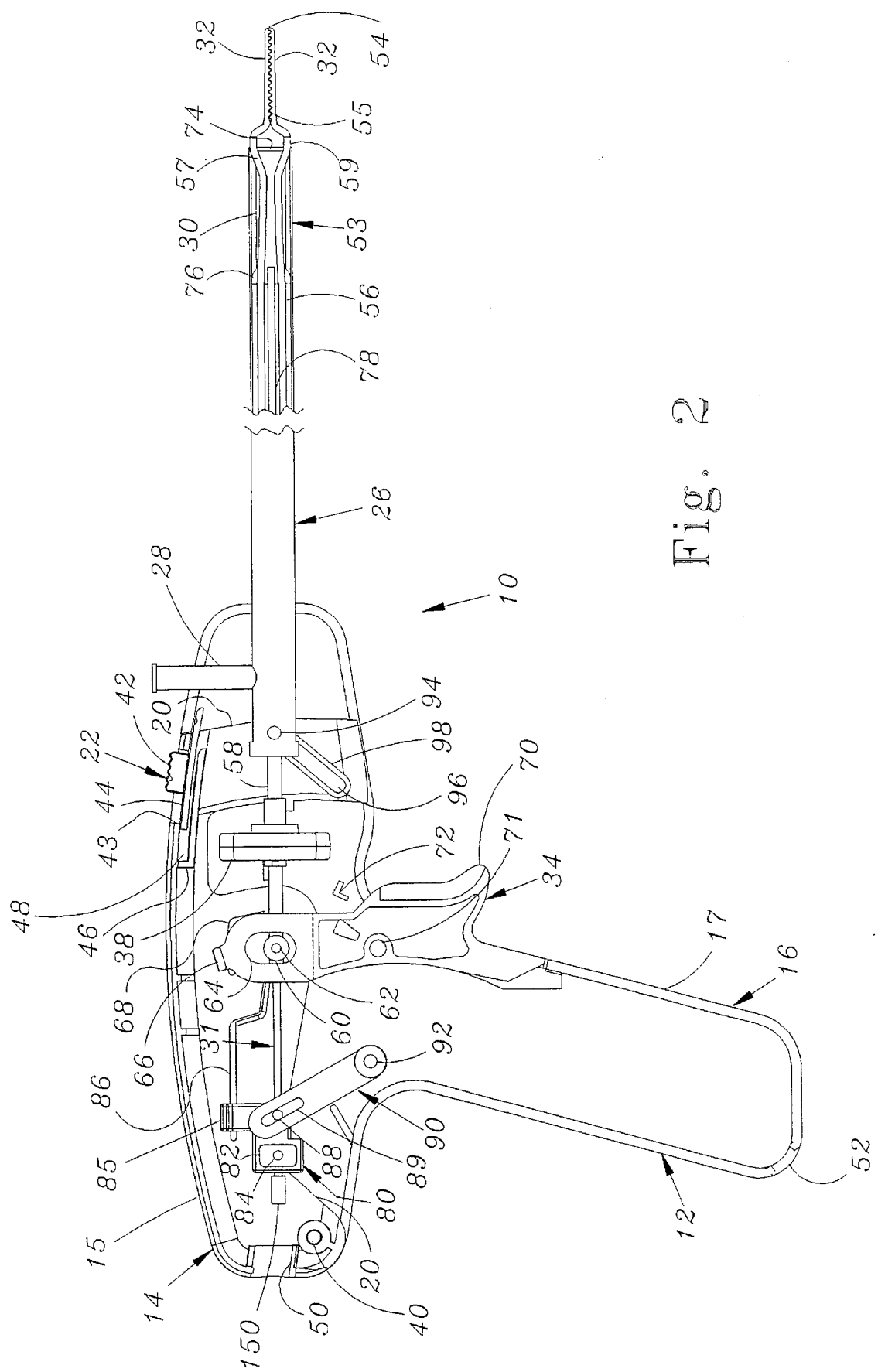
FIG. 2 is a side view of the surgical device shown in FIG. 1, with portions of the device removed to reveal details of the device.

FIG. 2 illustrates a view of surgical device 10 with portions of the device removed to reveal important features of the particular embodiment shown in FIG. 1. Specifically, the interior components of handle 12 are revealed by removal of one side of handle cover 14 and one side of handle body 16. Also, details relating to blade 30 and jaws 32 are revealed by presenting a portion of elongated sheath 26 in cross section.

Referring to FIG. 2, handle cover 14 is formed by two side halves 15 (only one shown) and handle body 16 is formed by two side halves 17 (only one shown). Handle cover 14 and handle body 16 of handle 12 are connected at a cover pivot 40 which is preferably molded into interior surfaces of handle 12. Handle cover 14 is locked to handle body 16 along contact line 20 with cover lock 22.

Cover lock 22 is provided with a contact surface 42 and a slide lock portion 44. Slide lock portion 44 is mounted within a cover lock channel 48 formed by a cover lock rib 46 which forms an integral part of both halves 15 of molded handle cover 14. Contact surface 42 is preferably ribbed so that it is more easily gripped by an operator's finger. Contact surface 42 extends through a cover lock opening 43 so that cover lock 22 can be moved between a forward position which engages a portion of handle body 16 and a rearward position which permits relative movement between handle cover 14 and handle body 16.

Access to the interior of handle 12 is provided by an access port 50 which is preferably molded into both halves 15 of handle cover 14. Access port 50 provides access for disengagement of a blade assembly mounted within handle 12 of surgical device 10, as will be described. Also, a bipolar plug mounting port 52 is provided in handle body 16 of handle 12 for mourning of bipolar plug 24 as shown in FIG. 1. Bipolar plug mounting port 52 is preferably molded into both halves 17 of handle body 16.

Opposed jaws 32 are shown in FIG. 2 in a closed position, wherein at least jaw tips 54 of opposed jaws 32 contact one another. Opposed jaws 32 are provided with serrations or teeth 55 which preferably mate as shown. Tongs 56 extend from opposed jaws 32 and each tong 56 includes ramped surfaces 57 for contacting an end of elongated sheath 26. Opposed jaws 32 and tongs 56 are preferably integrally formed from stainless steel.

Electrical insulation 59 is preferably provided on at least a portion of tongs 56 to prevent a short circuit between tongs 56 and elongated sheath 26. Electrical insulation 59 is preferably formed from plastic heat shrink tubing that is placed over tongs 56 and shrunk onto the outside surfaces of tongs 56 by application of heat. Electrical insulation 59 is optionally a coating applied to tongs 56 by use of known coating techniques.

Tongs 56 are connected to a tong tube 58, preferably formed from stainless steel, which extends through elongated sheath 26 and into an interior region of handle 12. Tong tube 58 is mounted to trigger 34 by means of a tong tube lock 60. Tong tube lock 60 is a cylindrical or spherical component, preferably formed from stainless steel, that is fixed to tong tube 58 by means of a set screw 62. A slot 64 in trigger 34 captures tong tube lock 60.

Trigger 34 also includes trigger guides 66 positioned to travel along and adjacent to trigger ribs 68 formed on an interior surface of both halves 15 of handle cover 14. Trigger ribs 68 are preferably molded into halves 15 and protrude toward a central region of handle 12.

Trigger 34 is provided with a finger contact surface 70 and is pivotally mounted to handle body 16 by means of trigger pivot studs 71 that are received within recesses in both halves 17 of handle body 16. Depression of finger contact surface 70 toward handle body 16 of handle 12 causes rotation of trigger 34 about trigger pivot studs 71, thereby causing advancement away from handle 12 of tong tube lock 60, tong tube 58, tongs 56 and opposed jaws 32.

A preferred embodiment of trigger 34 is described in co-pending application Ser. No. 08/527,127, filed Sep. 12, 1995. Trigger 34 is preferably a molded plastic or ceramic component but is optionally formed from many other insulating materials. For example, a liquid crystal polymer (LCP) such as VECTRA A530, available from Hoechst Celanese Corporation, is optionally used. Alternatively, trigger 34 is formed from any material that is preferably capable of withstanding repeated sterilizations.

Trigger 34 is preferably provided with external blade actuation lever limits 112 (FIG. 6) which are positioned on both sides of trigger 34 to limit the advancement of blade 30. Limits 112 extend through openings in both halves 17 of handle body 16. When external blade activation levers 36 contact limits 112 (as shown in FIG. 1), internal blade actuation levers 90 are stopped and blade 30 advancement is limited.

Advancement of opposed jaws 32 permits opposed jaws 32 to open and separate radially outwardly from one another as ramped surfaces 57 of tongs 56 slide along the end of elongated sheath 26. In other words, opposed jaws 32 are biased away from one another by the shape of tongs 56. Ramped surfaces 57 of tongs 56 permit separation of opposed jaws 32 as the tongs 56 are advanced from the end of elongated sheath 26. Similarly, retraction of tongs 56 into elongated sheath 26 forces opposed jaws 32 to move toward one another as ramped surfaces 57 of tongs 56 ride along the end of elongated sheath 26.

A trigger limiting boss 72 is provided on at least one interior surface of handle body 16 to limit the forward movement of the upper portion of trigger 34, thereby limiting the advancement of tong tube 58, tongs 56 and opposed jaws 32. Trigger 34 is preferably biased into the position shown in FIG. 2 by a torsion-type spring (not shown) that is connected to handle body 16 and that contacts a bottom portion of trigger 34.

A blade assembly 150, of which blade 30 is a part, is releasably mounted within handle 12 of surgical device 10 and extends through elongated sheath 26. Blade 30 is provided with a cutting edge 74 at its forward edge and with blade protrusions 76 at a rearward portion. Blade protrusions 76 extend radially adjacent an inside surface of elongated sheath 26.

Cutting edge 74 permits mechanical cutting or severance of coagulated or cauterized tissue as blade 30 is advanced against tissue that is gripped between opposed jaws 32. Blade protrusions 76 position blade 30 within elongated sheath 26 and prevent rotational movement of blade 30 with respect to opposed jaws 32.

Blade protrusions 76 on blade 30 also prevent removal of blade 30 and blade assembly 150 from surgical device 10 during normal operation of surgical device 10. Specifically, even when opposed jaws 32 are in an open position during use of surgical device 10 during a surgical procedure as shown in FIG. 1, blade protrusions 76 prevent blade 30 from passing between opposed jaws 32 and prevent removal of blade assembly 150 from the end of elongated sheath 26. In other words, the distance between the outermost surfaces of blade protrusions 76 is greater than the distance between jaw tips 54 when opposed jaws 32 are opened. This feature prevents removal of blade assembly 150 from elongated sheath 26 of surgical device 10 if blade assembly 150 is inadvertently released from handle 12.

Blade 30 of blade assembly 150 is mounted, preferably by means of a weld or braze, to a blade shaft 78. Blade assembly 150 extends through elongated sheath 26, within tong tube 58, and into the interior of handle 12. Blade assembly 150 is engaged by a blade assembly mounting tube 31, which extends toward elongated sheath 26 and into a rearward portion of tong tube 58. Tube 31 is securely mounted within handle 12 by connection to a movable blade lock holder 80. Preferred embodiments of blade assembly 150 and blade assembly mounting tube 31 will be described with reference to FIGS. 3 and 4.

A preferred embodiment of blade lock holder 80 is described in co-pending application Ser. No. 08/527,127, filed Sep. 12, 1995. Blade lock holder 80 is preferably formed from the same material as trigger 34, described above. Blade lock holder 80 is optionally formed from any suitable material but should be capable of withstanding repeated sterilization procedures.

Blade assembly mounting tube 31 is connected to blade lock holder 80 by means of a blade lock 82 secured to tube 31 by means of a set screw 84. Blade lock 82 is preferably a stainless steel cylinder with a passage to accommodate blade assembly mounting tube 31. Tightening of set screw 84 captures blade assembly mounting tube 31 in blade lock 82. Blade lock holder 80 is provided with blade lock holder guides 85 which are positioned to travel along and adjacent to blade lock ribs 86 formed on interior surfaces of both halves 15 of handle cover 14. Blade lock holder 80 is also provided with a blade lock holder stud 88.

Blade lock holder stud 88 is positioned for travel within a slot 89 of internal blade actuation levers 90 (only one is shown in FIG. 2). Internal levers 90 are mounted within handle body 16 by means of a pivot 92 received in recesses in the surfaces of handle body 16. Internal blade actuation levers 90 are connected through the wall of handle body 16 to external blade actuation levers 36 at pivots 92.

As external blade actuation levers 36 are advanced toward distal end 53 of elongated sheath 26, internal blade actuation levers 90 are rotated a corresponding distance about pivots 92, thereby advancing blade lock holder 80, blade assembly mounting tube 31 and blade assembly 150, including blade shaft 78, blade 30 and cutting edge 74. Internal blade actuation levers 90 are biased, preferably by a spring (not shown), toward the position shown in FIG. 2 with blade 30 and cutting edge 74 within distal end portion 53 of elongated sheath 26.

FIG. 2 also reveals that the portion of elongated sheath 26 mounted within handle 12 has a female luer lock 28 mounted thereon and communicating with an interior of elongated sheath 26 for cleaning purposes. Elongated sheath is also provided with sheath studs 94 (only one shown) which are positioned for mounting within sheath stud channels 96 formed by sheath stud ribs 98 which are preferably molded onto interior surfaces of both halves 15 of handle cover 14. As will be made clear with reference to FIG. 7, retraction of elongated sheath 26 into handle 12 causes upward movement of handle cover 14 as sheath studs 94 travel within sheath stud channels 96.

A preferred embodiment of elongated sheath 26 is described in co-pending application Ser. No. 08/527,127, filed Sep. 12, 1995. A proximal end portion of elongated sheath 26 is optionally provided with a groove for mounting a sheath seal (not shown) for preventing cleaning fluids or gases from traveling from the interior of elongated sheath 26 into the interior of handle 12. Such a sheath seal also acts to maintain insufflation pressure in the operative area and prevents the passage of blood and tissues through the elongated sheath and into the interior of handle 12.

Elongated sheath 26 is provided with a lumen which accommodates blade assembly 150, tongs 56 and tong tube 58. Elongated sheath 26 is preferably formed from stainless steel, and most preferably from type 304 stainless steel, but any suitable material is contemplated.

Details of several components of surgical device 10 shown in FIG. 2 will now be described in detail with reference to FIGS. 2A, 2B, 3, 4 and 5. Details of embodiments of these components are described merely for illustration. It should be appreciated that these components are interchangeable with alternative components or their equivalents.

FIGS. 2A and 2B are enlarged views of distal end portion 53 of elongated sheath 26 from the side and from the top, respectively. Opposed jaws 32 are shown in a closed position and contact one another at jaw tips 54. Also, blade 30 is shown in its advanced position wherein blade cutting edge 74 of blade 30 nearly contacts jaw tips 54 (best seen in FIG. 2B). It can be seen that blade protrusions 76 are adjacent to or contacting an inner surface of elongated sheath 26, thereby centering blade shaft 78 as it is reciprocated with blade 30 within elongated sheath 26.

The contour of tongs 56 is clearly shown in FIG. 2A. Ramped surfaces 57 of tongs 56 are preferably covered with electrical insulation 59 to provide protection against a short circuit between tongs 56 and elongated sheath 26. Contact between ramped surfaces 57 of tongs 56 and a distal edge 100 of elongated sheath 26 maintains opposed jaws 32 in a closed position when tongs 56 are retracted into elongated sheath 26. It can be seen, however, that ramped surfaces 57 on tongs 56 permit opposed jaws 32 to open and to separate as the outwardly biased tongs 56 are advanced in a direction away from handle 12.

FIG. 2B clearly shows that blade cutting edge 74 of blade 30 approaches, but does not contact, opposed jaws 32. The forward travel of blade 30 is restricted (by limits 112 on trigger 34) in relationship to opposed jaws 32 so that blade 30 and opposed jaws 32 never contact one another at blade cutting edge 74. Prevention of contact between blade cutting edge 74 and opposed jaws 32 helps to assure that the cutting edge will not be damaged during use.

Figure 3:
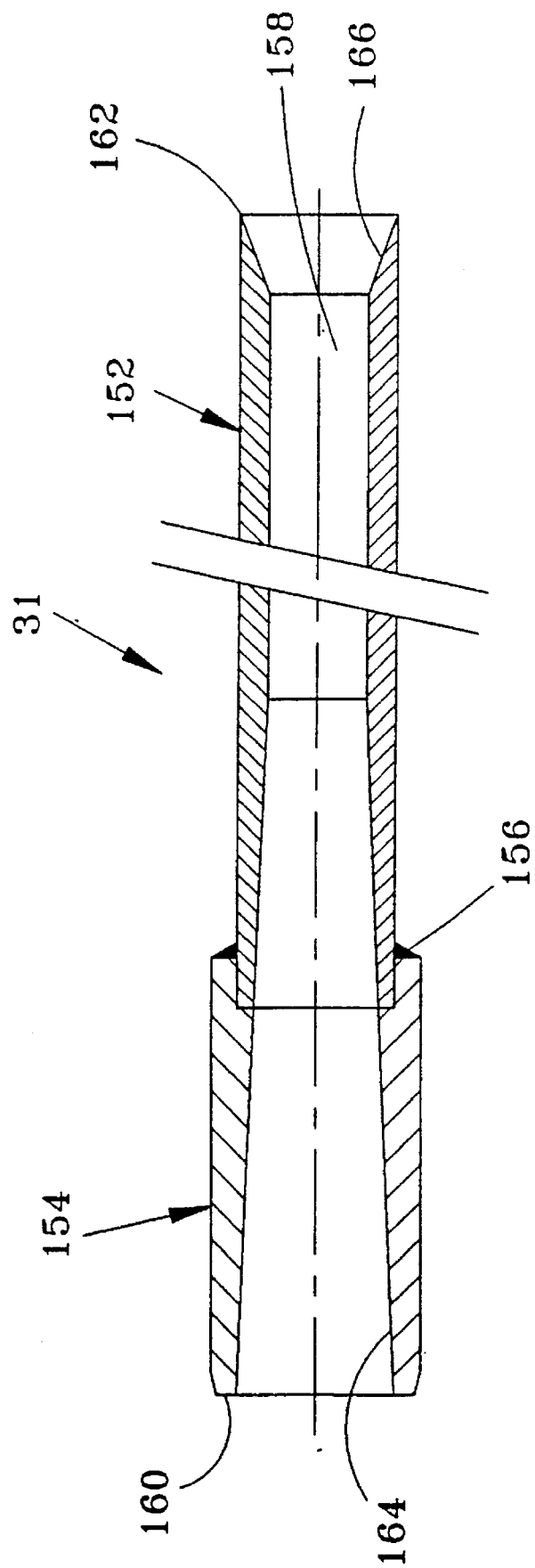
FIG. 3 is a cross-sectional side view of an embodiment of a component of the surgical device shown in FIG. 2.

FIG. 3 illustrates one preferred embodiment of blade assembly mounting tube 31, which is adapted for secured mounting within blade lock holder 80 by means of blade lock 84 and set screw 82. Blade assembly mounting tube 31 has a distal end portion 152 connected to a proximal end portion 154 by means of a braze or weld 156. Blade assembly mounting tube 31 defines a passage 158 which is sized and shaped to receive a mounting portion of blade assembly 150, as will be described hereinafter. Mounting tube 31 has a proximal end surface 160 and a distal end surface 162. A taper 164 is provided between passage 158 and proximal end surface 160. Similarly, a taper 166 is provided between passage 158 and distal end surface 162.

Blade assembly mounting tube 31 is preferably formed from stainless steel such as type 303 or type 304 stainless steel. The surfaces of tube 31 are most preferably hard-coated with titanium nitride (TiN), especially the surfaces defined by passage 158, proximal end surface 160 and distal end surface 162, for reasons that will be made clear. Although mounting tube 31 is shown in FIG. 3 as an assembly of two components, mounting tube 31 is optionally formed from one piece of steel or other suitable material.

Taper 166 adjacent distal end surface 162 of mounting tube 31 is adapted to receive a portion of blade assembly 150. Also, proximal end surface 160 of mounting tube 31 is adapted to engage a portion of blade assembly 150. These features will become clear as blade assembly 150 is described with reference to FIG. 4.

Figure 4:
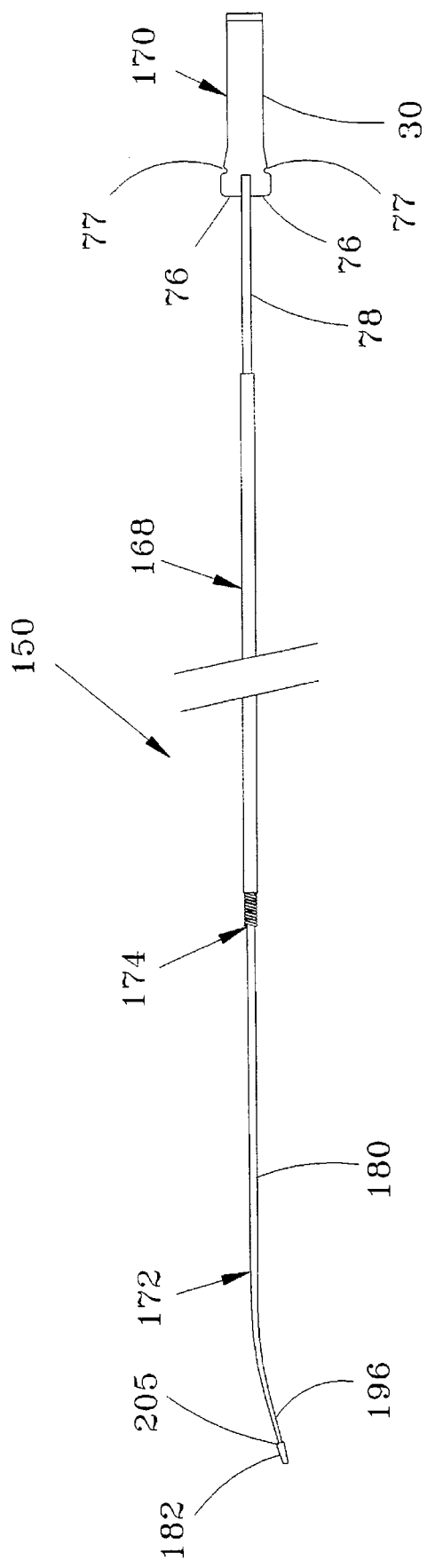
FIG. 4 is a side view of an embodiment of a subassembly of the surgical device shown in FIG. 2.

Referring to FIG. 4, a preferred embodiment of blade assembly 150 is illustrated. Blade assembly 150 has a central portion 168 connected at its distal end to a blade portion 170 and connected at its proximal end to a mounting portion 172.

A compression spring 174 is provided on mounting portion 172 adjacent central portion 168. Compression spring 174 is preferably a spring-temper type 302 stainless steel coil spring, but is optionally formed from any suitable material. Compression spring 174 most preferably has a load of about 2 lbs. and a rate of about 20 lbs. per inch, although any suitable spring with any suitable spring load and spring rate is optionally substituted.

Mounting portion 172 is provided with a mounting shaft 180 which terminates with a catch 182. Blade portion 170 includes blade 30 (introduced with reference to FIG. 1) which is connected to central portion 168 of blade assembly 150 by means of blade shaft 78 (introduced with reference to FIG. 2).

A preferred embodiment of blade assembly 150 is described in co-pending application Ser. No. 08/526,740, filed Sep. 12, 1995. Mounting shaft 180 is provided with a bend at a location between compression spring 174 and catch 182. Mounting shaft 180 is also provided with a taper 196 leading to catch 182. A shoulder 205 is formed by catch 182 and taper 196.

Catch 182 and mounting shaft 180 are provided with diameters suited to fit within passage 158 of blade assembly mounting tube 31 (shown in FIG. 3). Shoulder 205 on catch 182 is shaped to provide frictional engagement with proximal end surface 160 of blade assembly mounting tube 31. Also, referring to FIGS. 3 and 4, the distance between shoulder 205 on catch 182 and compression spring 174 (when compression spring 174 is in a compressed state) preferably corresponds to the length between proximal end 160 and distal end 162 of mounting tube 31.

Blade portion 170 is provided with blade 30 having two radial protrusions 76 and two indents 77, the significance of which will be made clear. Blade portion 170 is preferably formed from stainless steel but is optionally formed from any qualifying material capable of providing a sharp cutting edge 74 to sever tissue.

Figure 5:
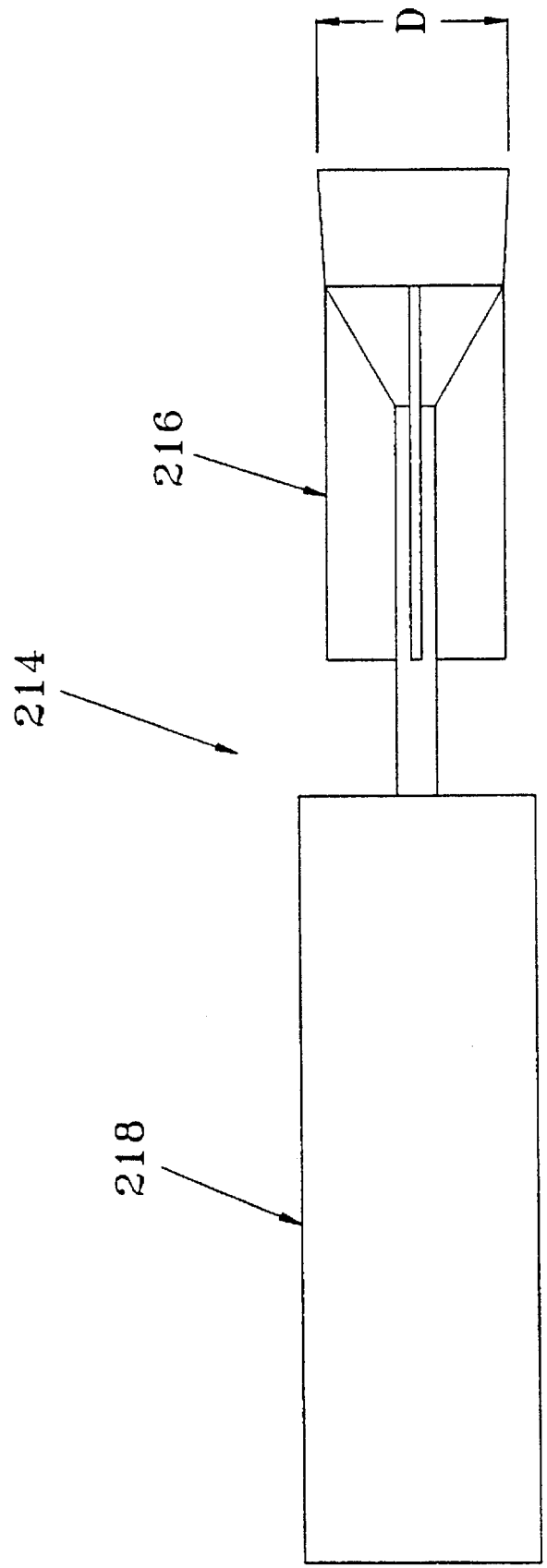
FIG. 5 is a side view of an embodiment of an optional release tool assembly adapted for use with the surgical device shown in FIG. 2.

FIG. 5 illustrates features of an optional blade assembly release tool generally designated by the numeral "214" that is adapted for releasing blade assembly 150 from surgical device 10. Specifically, release tool 214 is adapted for insertion through access port 50 at the rear portion of handle 12. Release tool 214 is shaped to engage catch 182 to release blade assembly 150 from within blade assembly mounting tube 31.

Release tool 214 is provided with a forward component 216 and a rearward component 218. Forward component 216 is provided with a diameter D sized to fit within access port 50 (shown in FIG. 2) for engagement with tube assembly 150. Rearward component 218 is primarily a grip for tool 214. Further details of release tool 214 are provided in co-pending application Ser. No. 08/526,740, filed Sep. 12, 1995.

Figure 6:
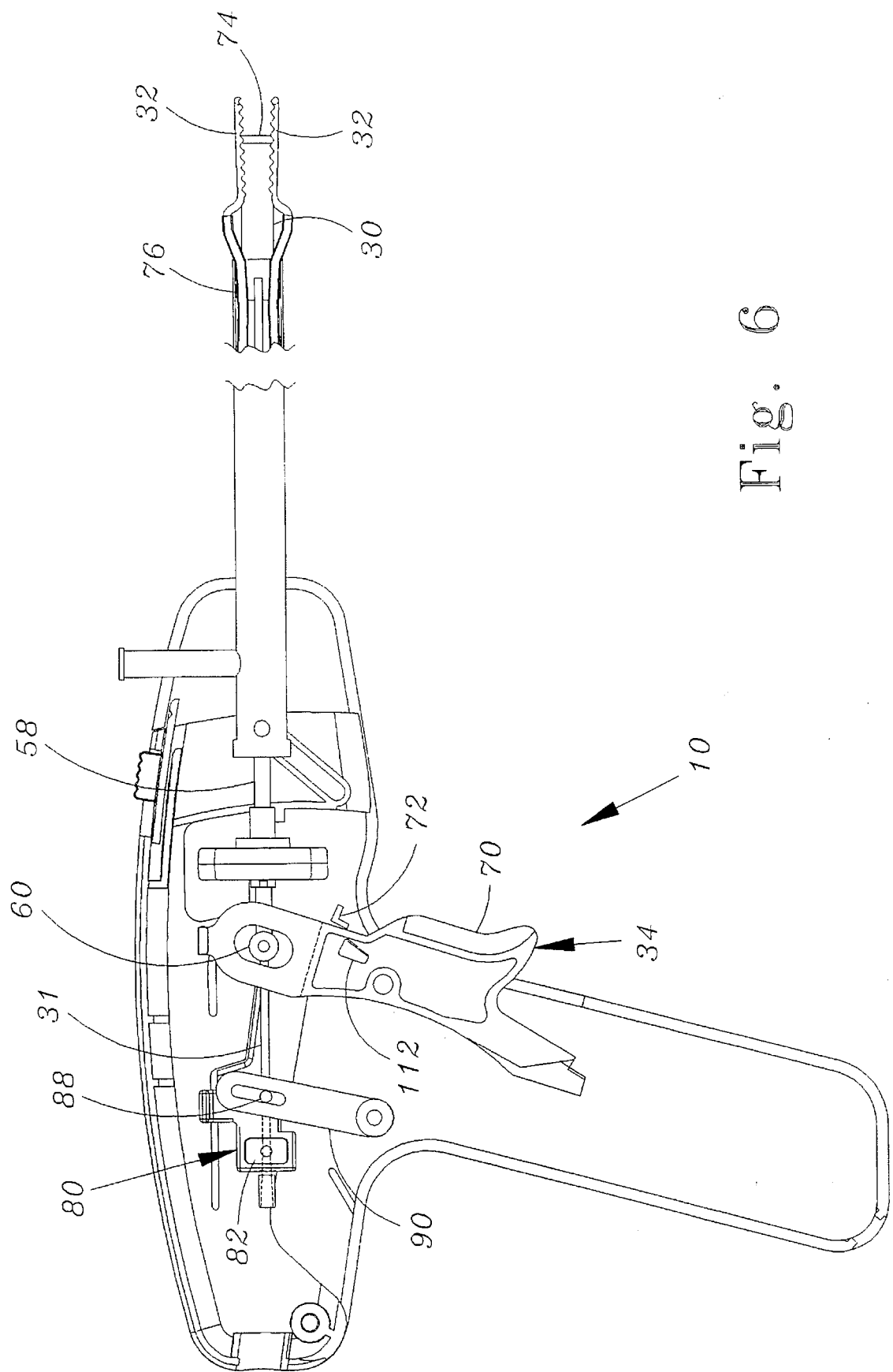
FIG. 6 is a side view of the surgical device shown in FIG. 2 in a blade-advanced, jaws-opened and cover-closed position.

Referring now to FIG. 6, reusable surgical device 10 is shown in a jaw-opened and blade-advanced position, similar to the position of surgical device 10 shown in FIG. 1. In this position, finger contact surface 70 of trigger 34 is depressed toward handle 12, thereby causing tong tube lock 60, tong tube 58 and tongs 56 to advance. Advancement of tongs 56 causes opposed jaws 32 to open and separate from one another. Trigger 34 is shown to be in contact with trigger limiting bosses 72, which are formed on inside surfaces of both halves 17 of handle body 16 to limit the rotation of trigger 34 with respect to handle 12.

Although not shown in FIG. 6, external blade actuation levers 36 are advanced to their forward-most position, contacting external blade actuation lever limits 112 on trigger 34. In this position, internal blade actuation levers 90 are advanced as is blade lock holder 80 and blade lock 82. This action advances mounting tube 31, blade assembly 150 and blade 30, but maintains blade protrusions 76 of blade 30 within the distal end portion 53 of elongated sheath 26.

Blade assembly 150 cannot be removed from surgical device 10 even when surgical device 10 is in the position illustrated in FIG. 6. Although opposed jaws 32 are open, blade protrusions 76 are unable to pass between opposed jaws 32 and blade assembly 150 cannot be removed from surgical device 10 through the distal end portion 53 of elongated sheath 26. Also, blade assembly 150 cannot be removed from surgical device 10 through access port 50 at the back end of handle 12 because blade 30 cannot fit within tong tube 58. Finally, blade assembly 150 is securely mounted within blade assembly mounting tube 31. Accordingly, blade assembly 150 cannot be removed from surgical device 10 in the position shown in FIG. 6.

Figure 7:
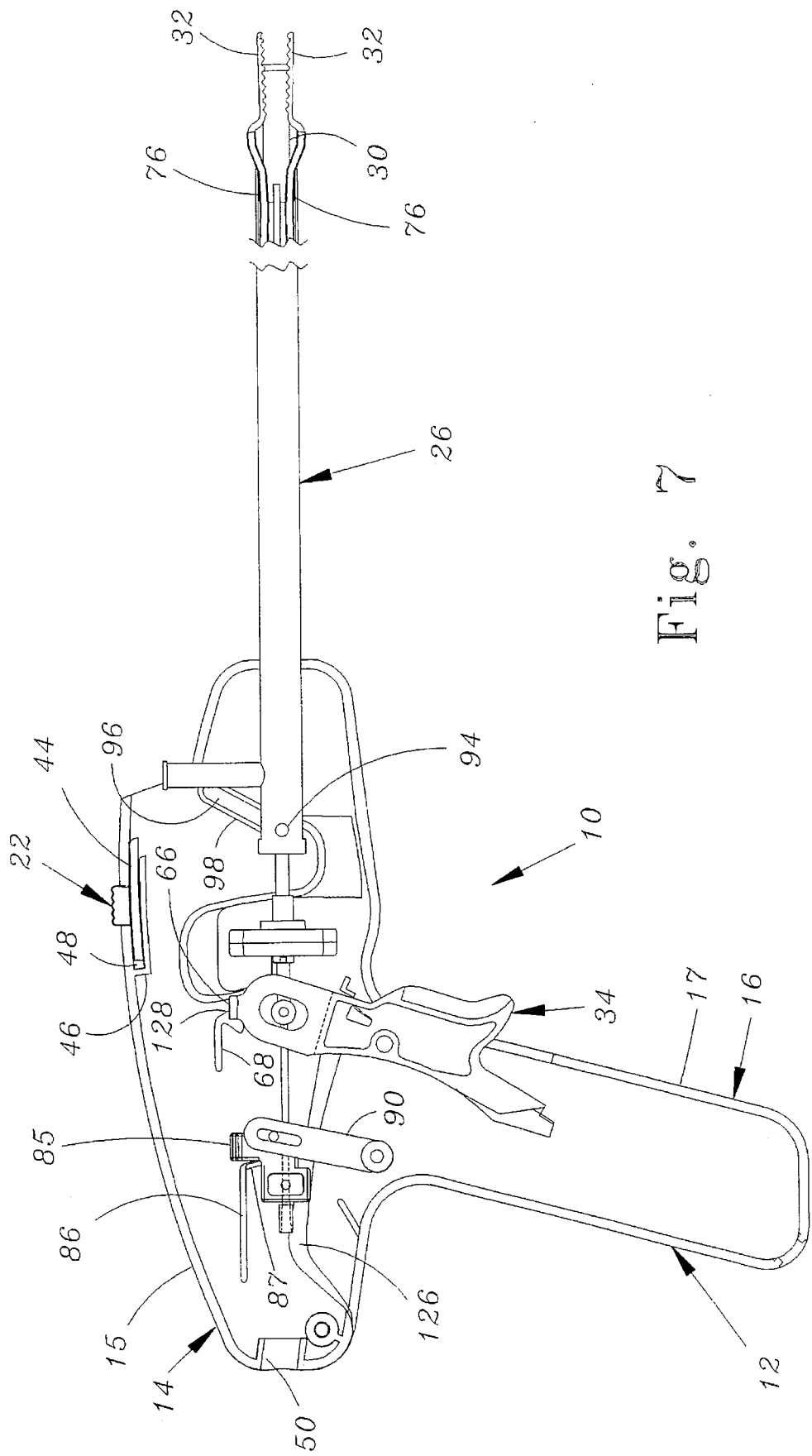
FIG. 7 is a side view of the surgical device shown in FIG. 2 in a blade-advanced, jaws-opened, cover-opened and sheath-retracted position.

Referring to FIG. 7, surgical device 10 is shown in an access position wherein blade assembly 150 is capable of being released and removed from surgical device 10. Specifically, trigger 34 and internal blade actuation levers 90 are in the positions described with reference to FIG. 6. Also, cover lock 22 is retracted by moving slide lock portion 44 rearwardly within cover lock channel 48 formed by cover lock rib 46, thereby disengaging handle cover 14 from handle body 16 and allowing handle cover 14 to rotate about cover pivot 40.

Also, elongated sheath 26 is retracted into handle 12 of surgical device 10. Travel of sheath studs 94 within sheath stud channels 96 formed by sheath stud ribs 98 causes handle cover 14 to open and rotate in a counterclockwise direction with respect to handle body 16.

Separation of handle cover 14 from handle body 16 creates a gap 126 between the components of handle 12. Also, notches 128 (one shown) provided in trigger ribs 68 capture trigger guides 66 of trigger 34, thereby locking trigger 34 in a depressed position and locking handle cover 14 in an open position. The bias of trigger 34 (created by the torsion spring) locks trigger guides 66 in notches 128 until trigger 34 is further depressed to release trigger guides 66 from notches 128. Also, downwardly extending portions 87 of blade lock ribs 86 maintain blade lock holder guides 85 and blade lock holder 80 in an advanced position, thereby locking blade 30 in its advanced position.

The retraction of elongated sheath 26 into handle 12 exposes a greater length of tongs 76. The outward bias of opposed jaws 32 permits farther separation of opposed jaws 32 from one another. In other words, retraction of elongated sheath 26 into handle 12 permits radial displacement of opposed jaws 32. In this displaced position, blade protrusions 76 on blade 30 are capable of passing between opposed jaws 32, thereby providing access for removal and replacement of blade assembly 150 through distal end portion 53 of elongated shaft 26.

Referring to FIGS. 2 and 6, the operation of surgical device 10 during a surgical procedure will be described. Surgical device 10 is introduced into an operative area through a cannula or other port in a patient while surgical device 10 is in a jaw-closed and blade-retracted position similar to the position illustrated in FIG. 2. Specifically, opposed jaws 32 are in a closed position contacting one another, blade 30 is retracted to a position within the distal end portion 53 of elongated sheath 26, and cover lock 22 is in a forward position to maintain handle cover 14 in contact with (and locked to) handle body 16 along contact line 20.

When tissue is to be cut, finger contact surface 70 of trigger 34 is depressed to advance and open opposed jaws 32. The opened jaws are then positioned on either side of the tissue to be severed. Finger contact surface 70 of trigger 34 is then released so that opposed jaws 32 close upon and grasp the tissue.

A foot pedal (not shown) is then depressed to introduce an electrical potential across opposed jaws 32 through bipolar plug 24 and wires (not shown) connected to tongs 56. This electrical potential is maintained until the tissue is satisfactorily cauterized or coagulated.

The tissue is then mechanically severed, while still within the grasp of opposed jaws 32, by pushing one or both external blade actuation levers 36 toward distal end 53 of elongated sheath 26 and advancing cutting edge 74 of blade 30 against the grasped, coagulated tissue. Cutting edge 74 of blade 30 cuts through the grasped tissue. An elongated dissection of tissue may be accomplished by repeating this process, moving opposed jaws 32 forward after each cut. Alternatively, opposed jaws 32 can be moved to another location within the operative area or surgical device 10 can be removed from the operative area entirely.

Operation of surgical device 10 between surgical procedures will now be described with reference to FIGS. 6 and 7. Between surgical procedures, it is necessary to clean and sterilize surgical device 10 and it is preferred to remove and replace blade assembly 150 so that a sharp and fresh cutting edge 74 is available for the next procedure.

In order to provide access to blade assembly 150 so that it can be removed and replaced, trigger 34 and internal blade actuation levers 90 are moved into the positions shown in FIG. 6. Cover lock 22 is then slid toward the rear of handle 12 to release handle cover 14 from handle body 16, as shown in FIG. 7. Elongated sheath 26 is then retracted into handle 12, thereby causing handle cover 14 to pivot with respect to handle body 16 about cover pivot 40.

Trigger guides 66 of trigger 34 are then captured within notches 128 formed in trigger ribs 68 by allowing trigger 34 to pivot slightly in the direction of its bias. In this position, blade assembly 150 is locked in an advanced position, opposed jaws 32 are locked in an open position, elongated sheath 26 is held in a retracted position, and handle cover 14 is maintained in a position separated from handle body 16.

Blade assembly 150 is then accessible for removal from distal end portion 53 of elongated sheath 26. Protrusions 76 on blade 30 of blade assembly 150 are able to pass between opposed jaws 32.

The preferred manner in which blade assembly 150 is released from handle 12 will now be described. Referring to the figures, blade assembly 150 is securely captured within blade assembly mounting tube 31. Specifically, as catch 182 of mounting portion 172 of blade assembly 150 is inserted through passage 158 in mounting tube 31, shoulder 205 of catch 182 engages proximal end surface 160 of blade assembly mounting tube 31. Also, distal end surface 162 of blade assembly mounting tube 31 is compressed against compression spring 174 of blade assembly 150. These features securely mount blade assembly 150 within tube 31. In other words, blade assembly mounting tube 31 is essentially captured between shoulder 205 and compression spring 174 of blade assembly 150.

Bend 184 in mounting shaft 180 of mounting portion 172 biases catch 182 in a radial direction. This bias encourages locking engagement between shoulder 205 and proximal end surface 160.

Blade assembly release tool 214 is shaped to release blade assembly 150. Specifically, when forward component 216 of tool 214 is inserted through access port 50 in handle 12, a tapered surface of tool 214 centers the tool over the rearward end of tube 31. A second tapered surface of tool 214 contacts catch 182.

Further advancement of tool 214 causes movement of catch 182 toward the axis of tube 31. This motion causes disengagement of shoulder 205 of catch 182 from proximal end surface 160 of blade assembly mounting tube 31. Such disengagement permits passage of catch 182 through mounting tube 31 and, in turn, release of blade assembly 150 from handle 12.

Blade assembly 150 can then be removed through the distal end 53 of elongated sheath 26 (and between opposed jaws 32) as described with reference to FIG. 7. A new blade assembly 150 can then be mounted within surgical device 10 by passing a mounting portion 180 of the new blade assembly 150 through the elongated sheath until the new catch 182 engages surface 160 of tube 31.

It is preferred for blade 30 and cutting edge 74 to be shielded or protected during removal and disposal to avoid injury and infection of an operator of surgical device 10. An embodiment of this invention provides a receptacle capable of providing such protection.

A preferred receptacle, adapted for use with reusable surgical device 10, will now be described with reference to FIGS. 8, 9A, 9B, 10A, 10B, 11 and 12. This invention is not intended to be limited to the specific embodiments shown in the figures. The invention is defined separately in the appended claims.

Figure 8:
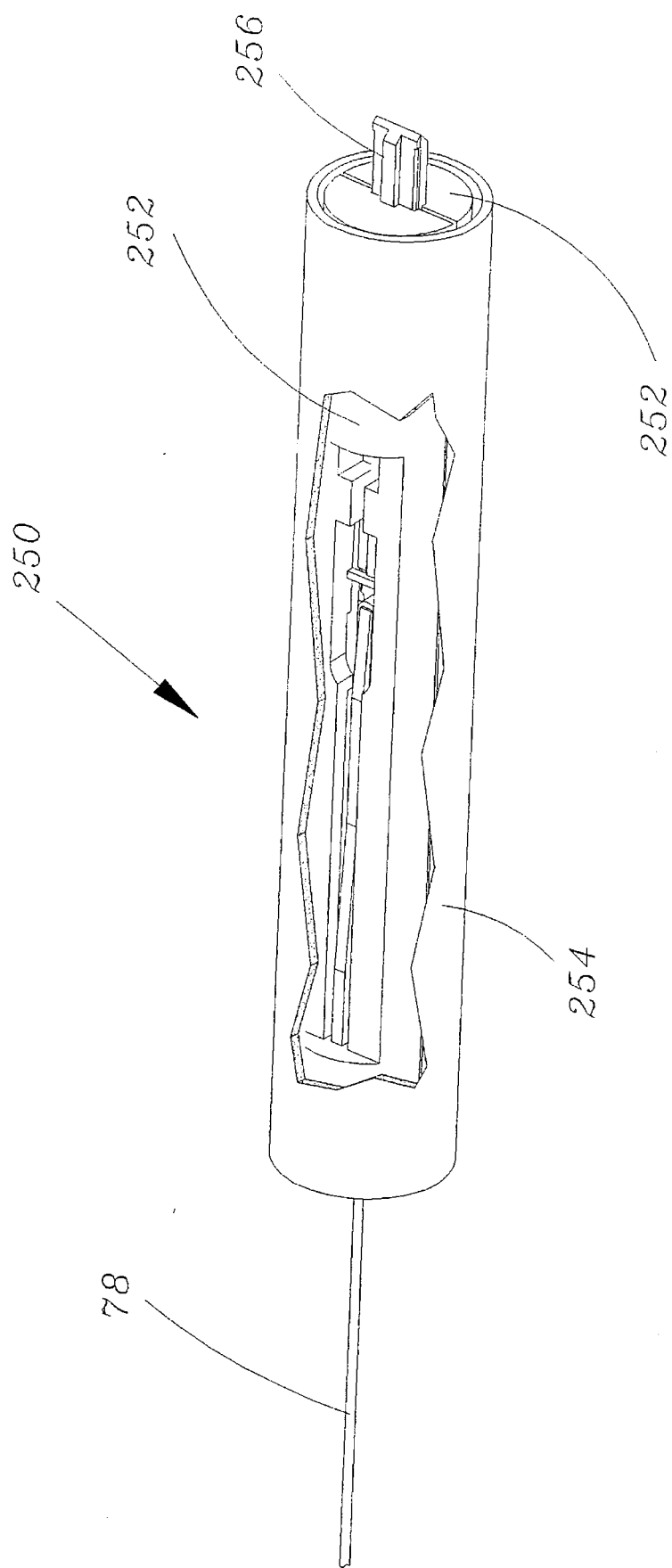
FIG. 8 is a perspective view of an embodiment of a blade assembly receptacle according to this invention, shown with a portion removed and with a blade assembly captured therein.

Referring to FIG. 8, the numeral "250" generally designates an embodiment of a receptacle according to this invention. Receptacle 250 is designed and adapted for use with reusable surgical device 10. Specifically, receptacle 250 is adapted to retrieve from surgical device 10 a used blade assembly for removal and disposal. Receptacle 250 is also adapted to contain a replacement blade assembly and facilitate installation of the replacement blade assembly into surgical device 10. Receptacle 250 is adapted to effectively perform these functions while shielding or protecting a tissue contacting tool such as blade 30 from contact by an operator of device 10 or one who supplies or discards new and used blade assemblies.

Receptacle 250 includes two housing halves 252 which are preferably identical to one another and which face one another to form a substantially cylindrical outer surface. A cover 254 is provided to hold housing halves 252 together and to substantially seal the interior of receptacle 250. Cover 254 is preferably formed from transparent plastic to permit visual inspection of the interior of receptacle 250. However, cover 254 is optionally formed from any metallic, plastic or other material capable of holding housing halves 252 in place. Also, cover 254 most preferably includes end caps (not shown) or other means for closing the ends of cover 254 and for providing a loose seal.

The numeral "256" generally designates a captured blade assembly, details of which are illustrated in FIGS. 9A and 9B. FIG. 9A illustrates captured blade assembly 256 in its assembled form. Captured blade assembly 256 includes a plunger 258 having a longitudinal plunger guide 260. Blade assembly 150 is shown mounted within plunger 258, wherein blade 30 is captured and cutting edge 74 (not shown) is encapsulated. An end surface 261 of blade shaft 78 is indicated, the significance of which will be described.

FIG. 9B illustrates captured blade assembly 256 wherein plunger 258 is shown in an open position to reveal important features of this embodiment. Plunger 258 has a blade receiving portion 262 and a cover portion 264 which are connected to one another at a living hinge 266. Blade receiving portion 262 includes longitudinal channels 268. Blade receiving portion 262 is also provided with a hole 270 to permit closure of plunger 258.

Blade receiving portion 262 is also provided with a cavity 272 shaped to receive at least a portion of blade 30 of blade assembly 150. Extending from the walls which form cavity 272 are arms 274 which terminate at detents 276. Detents 276 are positioned to capture blade 30.

Cover portion 264 of plunger 258 is provided with longitudinal ridges 278 which extend substantially the entire length of cover portion 264 and are positioned to fit within channels 268 of blade receiving portion 262. A stud 280 is provided on cover portion 264 and is positioned to mate with hole 270 in blade receiving portion 262 to hold plunger 258 in a closed position. A cavity 282 is formed in cover portion 264 to accommodate at least a portion of blade 30 when plunger 258 is in a closed position as shown in FIG. 9A. Accordingly, plunger 258 is closed by rotating cover portion 264 with respect to blade receiving portion 262 about living hinge 266 until stud 280 is engaged in hole 270 and ridges 278 are received on channels 268.

Figure 10A:
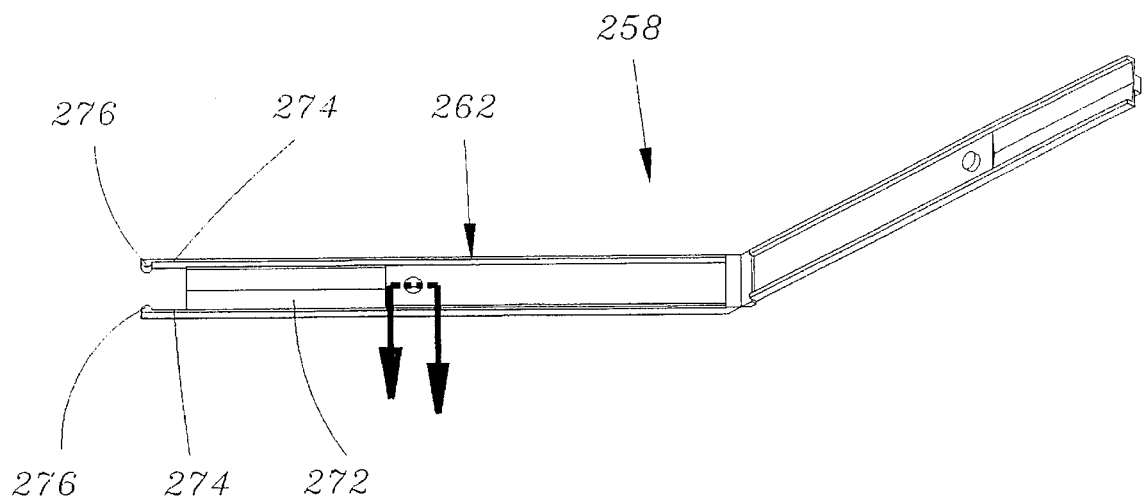
FIG. 10A is a perspective view of the component illustrated in FIG. 9B, without the blade assembly.
Figure 10B:
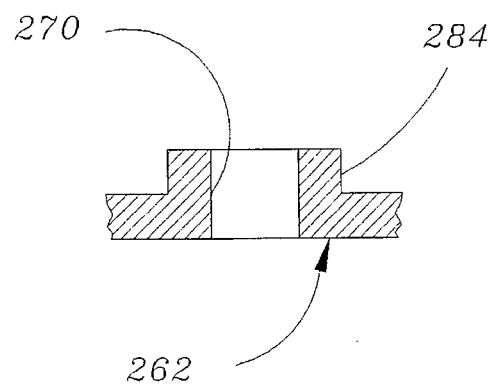
FIG. 10B is a top cross-sectional view of the component illustrated in FIG. 10A.

FIGS. 10A and 10B illustrate plunger 258 shown in an open position without blade assembly 150. The preferred shape of detents 276 on arms 274 of blade receiving portion 262 is more clearly illustrated. FIG. 10B is a top view of a portion of blade receiving portion 262 of plunger 258, illustrated in cross-section. A peg 284 is provided on blade receiving portion 262 at a position corresponding to hole 270. Peg 284 is not visible in FIG. 10A because it protrudes from the back of blade receiving portion 262 in that view. The significance of peg 284 will be described with reference to FIG. 11.

Plunger 258 is preferably formed from a plastic material, but any material capable of protecting blade 30 is contemplated. However, the material of plunger 258 is most preferably softer than the material of blade 30 to prevent damage to cutting edge 74 of the blade.

Figure 11:
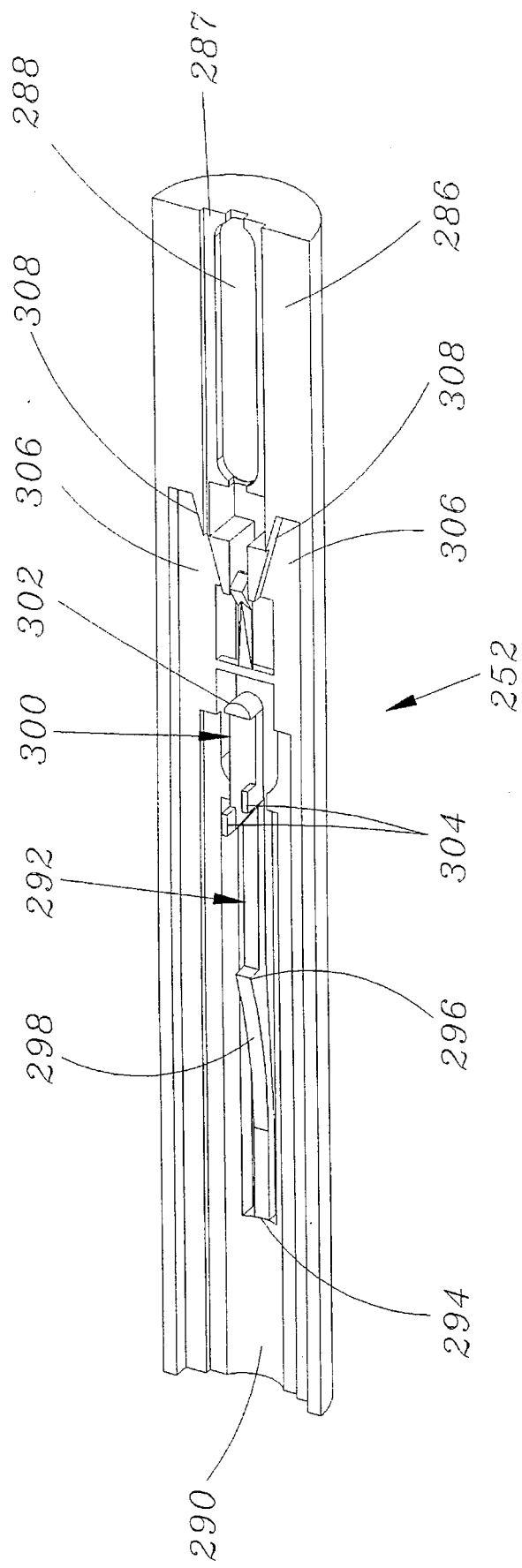
FIG. 11 is a perspective view of an embodiment of another component of the blade assembly receptacle illustrated in FIG. 8.

FIG. 11 illustrates details of one embodiment of housing half 252 adapted for use in receptacle 250. Housing half 252 is preferably a molded component, preferably formed from rigid plastic. Housing halves 252 (only one shown) are preferably identical to one another and designed to mate with one another so as to capture or engage captured blade assembly 256.

Housing half 252 has a face 286 in which a plunger channel 287 is formed to accommodate plunger 258. Also formed in face 286 is a peg channel 288 positioned to accommodate peg 284 (shown in FIG. 10B) for sliding movement within peg channel 288. Also formed in face 286 of housing half 252 is a sheath cavity 290 which is shaped and positioned to receive distal end portion 53 of elongated sheath 26.

A blade assembly capturing arm 292 is formed within housing half 252 and is connected adjacent to sheath cavity 290 by means of a living hinge 294. Blade assembly capturing arm includes a sheath contacting detent 296 having a ramped surface 298. Blade assembly capturing arm 292 is also provided with a head 300. Head 300 terminates at a blade assembly shaft grasp 302 at one end and is provided with staggered alignment detents 304 at an opposite end. Living hinge 294 permits movement of head 300 of blade assembly capturing arm 292 in a direction substantially perpendicular to the longitudinal axis of housing half 252 within an opening 295.

Also formed in face 286 of housing half 252 is a pair of jaw cavities 306 shaped and positioned to receive opposed jaws 32 of surgical device 10. Jaw cavities 306 are provided with ramped surfaces 308 along which tips 74 of opposed jaws 32 travel.

The significance of the details of housing half 252 shown in FIG. 11 will be made clear with reference to FIG. 12. However, the details of the embodiment shown in FIG. 11 can be modified in many ways to engage captured blade assembly 256 or in many additional ways to capture other types of tools adapted for releasable attachment within any reusable device.

Figure 12:
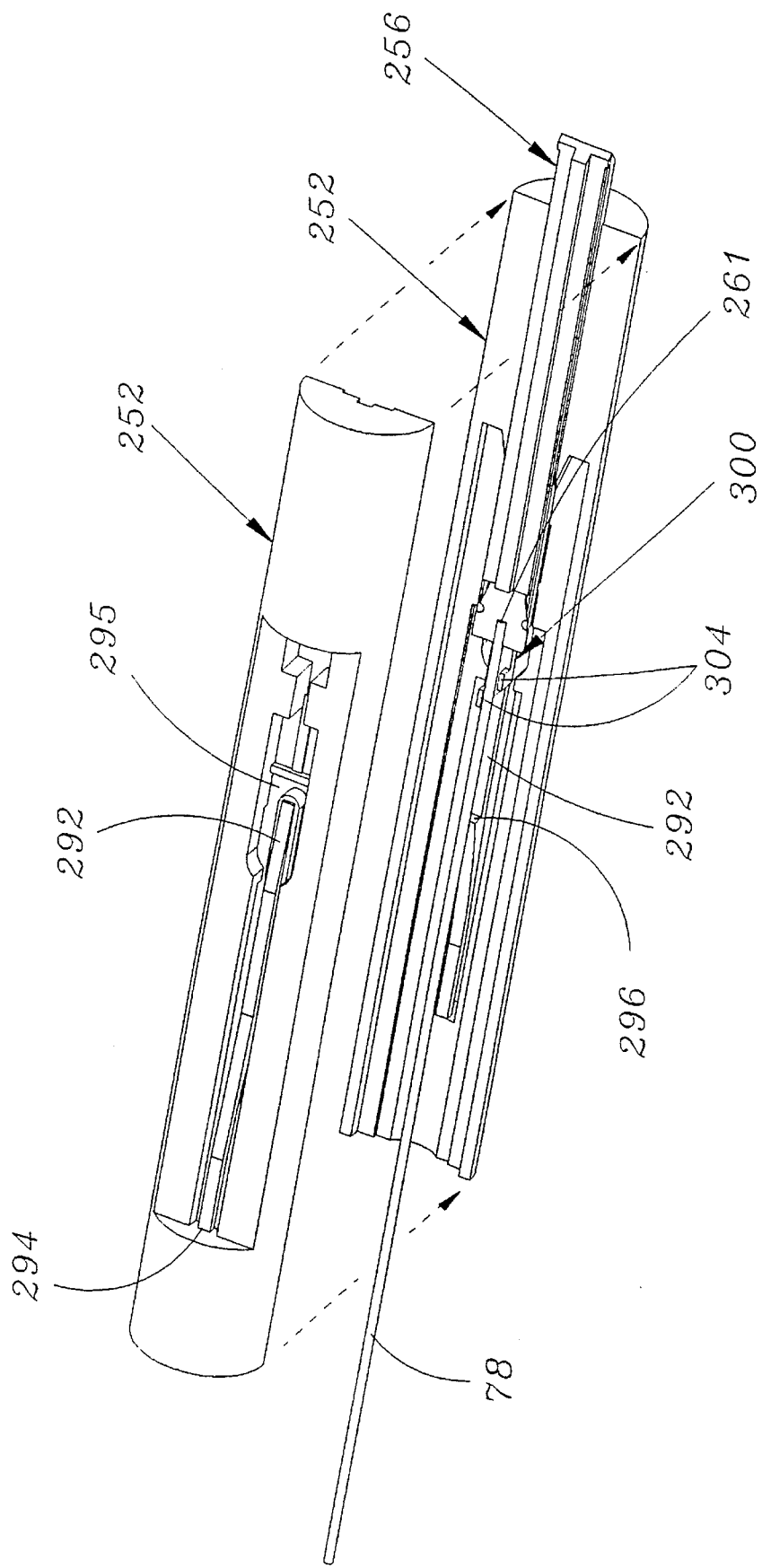
FIG. 12 is a perspective view of the component illustrated in FIG. 11, shown with the component illustrated in FIG. 10A and a blade assembly therein.

FIG. 12 illustrates both housing halves 252, one of which is shown with captured blade assembly 256 mounted in place (the "lower" housing half) and the other is shown in a position ready to enclose captured blade assembly 256 (the "upper" housing half). The view illustrating the back portion of upper housing half 252 illustrates a back portion of blade assembly capturing arm 292 and living hinge 294.

Captured blade assembly 256 is shown within lower housing half 252 to illustrate the relationship between housing half 252 and the captured blade assembly. Although not visible in this view, peg 284 of plunger 258 (FIG. 10B) is positioned within peg channel 288 of housing half 252, thereby permitting limited longitudinal movement of captured blade assembly 256. Staggered alignment detents 304 are positioned on both sides of blade shaft 78, thereby supporting the blade shaft and limiting the side-to-side movement of captured blade assembly 256. Although not visible, blade assembly shaft grasp 302 (FIG. 11) on head 300 of blade assembly capturing arm 292 engages end surface 261 of blade shaft 78. Once engaged, blade assembly shaft grasp 302 prevents movement of captured blade assembly 256 in the longitudinal direction toward the right-hand side of FIG. 12.

As described above, housing halves 252 are preferably identical to one another, most preferably formed in the same mold. Accordingly, staggered alignment detents 304 of upper housing half 252 compliment the detents of lower housing half 252 to provide additional support for blade shaft 78.

It can be seen that captured blade assembly 256 is indeed captured within receptacle 250 when the captured blade assembly is positioned between housing halves 252 and cover 254 is slid over housing halves 252 to hold them together.

The use of receptacle 250 with a new or replacement blade assembly 150 for insertion of the blade assembly into surgical device 10 will now be described with reference to the various figures. A replacement blade assembly 150 is installed in plunger 258 as shown in FIG. 9B by placing blade 30 within cavity 272 of blade receiving portion 262. Detents 276 on arms 274 are positioned within indents 77 on blade 30, thereby engaging blade 30 within cavity 272.

Captured blade assembly 256 (FIG. 9A) is formed by closing plunger 258 by inserting stud 280 on cover portion 264 into hole 270 of blade receiving portion 262 as cover portion 264 rotates with respect to blade receiving portion 262 about living hinge 266.

Captured blade assembly 256 is then positioned within lower housing half 252 (FIG. 12) by positioning peg 284 (FIG. 10B) within peg channel 288 (FIG. 11). Also, blade shaft 78 is positioned between staggered alignment detents 304 and end surface 261 of blade shaft 78 is positioned adjacent to blade assembly shaft grasp 302. Housing halves 252 are then positioned with face 286 of the lower half 252 adjacent to face 286 of the upper half 252. Cover 254 is then slid over housing halves 252 to hold them in place.

Seals and locking members (not shown) are optionally positioned adjacent the ends of cover 254 to seal the ends of cover 254 and lock cover 254 to housing halves 252. For example, polymeric or elastomeric caps are optionally positioned over the ends of cover 254. Such caps preferably have openings or slits to create seals about blade shaft 78 and captured blade assembly 256.

The installation of new blade assembly 150 in surgical device 10 will now be described. Distal end portion 53 of elongated sheath 26 is placed within sheath cavity 290 formed by housing halves 252. As sheath 26 is installed, the advancing sheath 26 "rides along" ramped surfaces 298 of sheath contacting detents 296. This action moves heads 300 of blade assembly capturing arms 292 in a radially outward direction. Outward movement of heads 300 releases engagement between blade assembly shaft grasps 302 and end surfaces 261 of blade shaft 78. Outward movement of heads 300 also disengages staggered alignment detents 304 from blade shaft 78. Blade assembly 150 is thereby released from blade assembly capturing arms 292. Also, blade 30 is then free to move toward the left-hand side of FIG. 12 and beyond staggered alignment detents 304.

Also, as opposed jaws 32 of surgical device 10 are advanced within receptacle 250, tips 74 of opposed blades 32 "ride along" ramped surfaces 308 of jaw cavities 306. This motion separates opposed jaws 32 farther from one another, thereby permitting protrusions 76 on blade 30 to pass between opposed jaws 32.

After elongated sheath 26 is inserted in receptacle 250 (until elongated sheath 26 contacts an innermost edge of sheath cavity 290), replacement blade assembly 150 is ready for releasable engagement within surgical device 10. Plunger 258 of captured blade assembly 256 is grasped by an operator of receptacle 250 and is pushed toward elongated sheath 26. Although movement of captured blade assembly 256 within receptacle 250 is limited by peg 284 and channel 288, the travel is sufficient to provide mounting of blade assembly 150. Specifically, blade assembly 150 is inserted into surgical device 10 until shoulder 205 on catch 182 (FIG. 4) engages proximal end surface 160 of mounting tube 31 (FIG. 3). Channel 288 is optionally provided with a taper so that plunger 258 is held in a position suitable to engage blade assembly 150 within device 10. The engagement between detents 276 on arms 274 of plunger 258 and indents 77 of blade 30 is stronger than the force required to install blade assembly 150 into surgical device 10.

Release of receptacle 250 from sheath 26 and blade assembly 150 is accomplished by pulling receptacle 250 away from the sheath. The engagement of blade assembly 150 within surgical device 10 is stronger than the engagement between detents 276 on arms 274 of plunger 258 and indents 77 of blade 30. Accordingly, blade assembly 150 remains mounted within surgical device 10 as detents 276 are released from indents 77 of blade assembly 150. Receptacle 250 is then entirely removed from surgical device 10.

Use of receptacle 250 to remove a used blade assembly 150 from surgical device 10 will now be described with reference to the figures. An empty receptacle 250 is preferably provided with housing halves 252 within cover 254 together with any locking and sealing members and with an empty plunger (FIG. 10A) in a closed position. Accordingly, empty receptacle 250 is similar to that shown in FIG. 8, except that captured blade assembly 256 is replaced with an empty and closed plunger 258.

Such an empty receptacle is optionally provided with replacement blade kits for the operator's convenience. Also, an empty receptacle from an installed replacement blade is optionally retained by the operator for use during removal of the replacement blade after it has been used.

In order to remove a used blade assembly 150 from surgical device 10, surgical device 10 is first placed in the position shown in FIG. 7, with the blade advanced, trigger depressed, door open, and sheath retracted. Empty receptacle 250 is then placed over distal end portion 53 of elongated sheath 26 until the sheath contacts an innermost surface of sheath cavity 290. Heads 300 of blade assembly capturing arms 292 are moved radially outwardly and opposed jaws 32 of device 10 are separated within jaw cavities 306.

Empty plunger 258 is then grasped by an operator of device 10 and is advanced toward elongated sheath 26 while blade 30 is inserted into cavities 272 and 282 (FIG. 9B). Detents 276 on arms 274 of plunger 258 engage indents 77 on used blade 30.

Used blade assembly 150 is then released from surgical device 10. This is accomplished using release tool 214. Release tool 214 is inserted through port 50 of handle 12 of surgical device 10 and releases shoulder 205 on catch 182 of blade assembly 150 from proximal end surface 160 of tube 31. This allows passage of catch 182 through passage 158 in tube 31 so that used blade assembly 150 can be released from surgical device 10.

Used blade assembly 150 is then removed from surgical device 10 by removing receptacle 250 from elongated sheath 26. As sheath 26 exits receptacle 250, blade assembly capturing arms 292 return to their at-rest position so that staggered alignment detents 304 engage blade shaft 78 and grasps 302 engage blade shaft end surface 261. Also, blade 30 remains captured within plunger 258 by engagement between plunger detents 276 and blade indents 77. Blade assembly 150 is prevented from release from receptacle 250 by contact between the rear end of blade 30 and staggered alignment detents 304.

As mentioned with reference to FIG. 8, cover 254 of receptacle 250 is preferably transparent to aid the operator of device 10 in placement of empty plunger 258 over blade 30 of blade assembly 150. Specifically, the operator preferably views the relative positions of blade 30 and plunger 258 through cover 254 and through openings in housing halves 252.

When receptacle 250 is completely removed from surgical device 10 with used blade assembly 150, the receptacle and blade assembly can be handled without injury or infection of the operator and can be discarded without injury or infection of those handling the refuse. Also, after receptacle 250 and used blade assembly 150 are removed from surgical device 10, the surgical device is then ready to receive a new or replacement blade assembly or some other tool.

Many modifications can be made to the specific embodiments shown in the figures without departing from the spirit and scope of this invention. The configuration, materials and shapes of the components of the specific embodiment disclosed are optionally modified or replaced, depending upon specific intended uses of the surgical device and depending upon manufacturer preferences. The specific embodiments illustrated in the figures show components adapted for use with a specific replaceable tool and a specific reusable device. It must be appreciated that many modifications to these components are contemplated, depending upon the shape and nature of the tool to be removed and replaced as well as the shape and nature of the reusable device.

For example, blade assembly 150 is optionally replaced with any component or tool (or group of components or tools) that is preferably replaced periodically or between surgical procedures, yet is mounted securely within the device during use. The blade assembly is optionally replaced with an electrode; a tissue manipulating tool; a stapler mechanism; tools that are difficult to sterilize; tools that are only effective for a single use or a limited member of uses; or any other tool wherein removal and replacement of that tool, periodically or between each surgical procedure, benefits the overall effectiveness of the surgical device. Modification of the receptacle to accommodate any tool or component of any size and configuration is contemplated.

Also, this invention is optionally utilized with a surgical device adapted for use with interchangeable tools. Such interchangeable tools optionally take any form and are used for any purpose. For example, such interchangeable tools are optionally tissue cutting tools with various blade shapes or configurations wherein a specific blade shape is desirable for one procedure and a different blade shape is desirable for another procedure. Also, interchangeable tools optionally perform radically different functions—a tissue cutting tool is optionally removed from the device and replaced with an electrode, with a stapler, or with any other type of tool. Accordingly, this invention makes it possible to provide a universal and versatile receptacle for any number and type of surgical tools.

In fact, this invention relates to any type of device whatsoever, and is not intended to be limited to use with surgical devices. In any embodiment, this invention provides a receptacle adapted to contain a removable and replaceable component or tool of a reusable device.

What is claimed is:

1. A receptacle for holding an end portion of a tool, said receptacle being adapted to facilitate handling of said tool for installation of said tool into a reusable device or for removal of said tool from a reusable device, said receptacle comprising:

a receptacle body shaped to accommodate said end portion of said tool, said receptacle body having at one end a surface defining a passageway with a passageway axis positioned to receive said end portion of said tool; and a receiving member for receiving at least a portion of said end portion of said tool, said receiving member being engaged said receptacle body and positioned adjacent to an end of said receptacle body substantially opposite from said passageway, said receiving member being longitudinally movable with respect to said receptacle body along a member axis that substantially corresponds to said passageway axis, said receiving member having an external portion positioned for access from outside said receptacle body for manipulation of said receiving member, and said receiving member having an internal portion positioned within said receptacle body and means for releasably engaging said end portion of said tool to prevent longitudinal movement of said tool with respect to said receiving member.

2. The receptacle defined in claim 1, further comprising a receptacle cover shaped to substantially enclose said receptacle body.

3. The receptacle defined in claim 2, wherein at least a portion of said receptacle cover is transparent to permit inspection by an operator of said receptacle of relative positions between said internal portion of said receiving member and said end portion of said tool when said end portion of said tool is received in said passageway of said receptacle body.

4. The receptacle defined in claim 1, wherein said internal portion of said receiving member defines a cavity shaped to substantially surround said end portion of said tool to prevent contact between an operator of said receptacle and said end portion of said tool and to prevent damage to said end portion of said tool.

5. The receptacle defined in claim 1, wherein said end portion of said tool includes an engagement contour and said internal portion of said receiving member includes an engagement member positioned to engage said engagement contour.

6. The receptacle defined in claim 5, wherein an engagement force between said engagement member on said internal portion of said receiving member and said engagement contour on said end portion of said tool is (a) less than an installed force between said tool and said reusable device, said installed force maintaining a connection between said tool and said reusable device after said tool is installed in said reusable device, and (b) greater than an installation force between said tool and said reusable device, said installation force being required to install said tool in said reusable device.

7. The receptacle defined in claim 1, wherein said receptacle body is formed from two mating halves.

8. The receptacle defined in claim 1, wherein said receptacle further comprises a grasping member for grasping said end portion of said tool, said grasping member being positioned mounted within said receptacle body for movement between a relaxed position to grasp said end portion of said tool and a radially extended position to release said end portion of said tool.

9. A receptacle for holding an end portion of a tool, said receptacle being adapted to facilitate handling of said tool for installation or removal of said tool with respect to a reusable device having a manipulator with an operative end portion positioned adjacent to said tool after installation of said tool, said receptacle comprising:

a receptacle body shaped to accommodate said end portion of said tool and an operative end portion of a manipulator, said receptacle body having at one end a surface defining a passageway with a passageway axis positioned to receive said end portion of said tool and an operative end portion of a manipulator; and a receiving member for receiving at least a portion of said end portion of said tool, said receiving member being engaged by said receptacle body and position adjacent to an end of said receptacle body substantially opposite from said passageway, said receiving member being longitudinally movable with respect to said receptacle body along a member axis that substantially corresponds to said passageway axis, said receiving member having an external portion positioned for access from outside said receptacle body for manipulation of said receiving member, and said receiving member having an internal portion positioned within said receptacle body and means for releasably engaging said end portion of said tool to prevent longitudinal movement of said tool with respect to said receiving member.

10. The receptacle defined in claim 9, wherein said receptacle body includes an internal surface positioned to contact an operative end portion of a manipulator as an operative end portion of a manipulator is received in said passageway, said internal surface being shaped to displace an operative end portion of a manipulator in a radial direction relative to said passageway axis.

11. The receptacle defined in claim 10, wherein an operative end portion of a manipulator includes a pair of opposed jaws and said internal surface of said receptacle body includes a pair of angled surfaces, one for each opposed jaw, positioned to separate opposed jaws from one another in said radial direction a distance sufficient to permit passage of said tool between opposed jaws as opposed jaws are received in said passageway.

12. A method for removing a tool from a reusable device while preventing contact between an operator of a reusable device and an end portion of said tool, said method comprising the steps of;

(a) providing a receptacle having a surface defining a passageway shaped to receive said end portion of said tool, said receptacle also having a receiving member engaged by said receptacle for reciprocal longitudinal movement with respect to said receptacle, said receiving member having an end portion positioned within said receptacle that is shaped to releasably engage said end portion of said tool to present longitudinal movement of said tool with respect to said receiving member, and said receiving member having an end portion that is accessible from outside said receptacle for manipulating said receiving member;

(b) inserting said end portion of said tool into said passageway defined by said receptacle;

(c) moving said receiving member longitudinally with respect to said receptacle to releasably engage said end portion of said tool by manipulating said end portion of said receiving member that is accessible from outside said receptacle;

(d) releasing said tool from a reusable device; and (e) removing said tool, together with said receptacle, from a reusable device by moving said receptacle longitudinally with respect to a reusable device while retaining said end portion of said tool within said receptacle.

13. An article for containing an operative portion of a surgical blade, said operative portion of said surgical blade being substantially flat and having a cutting edge, said article comprising:

mating cover components having a closed position with said cover components contacting one another, wherein said cover components in said closed position define a cavity shaped to accommodate said operative portion of said surgical blade, said cover components also having an open position with at least a portion of one of said cover components separated from another one of said cover components, wherein said cover components in said open position provide access to said cavity; and a detent connected to at least one of said cover components and positioned to engage said surgical blade, said detent including a surface oriented to contact said surgical blade and prevent lengthwise movement of said surgical blade with respect to said article;

wherein said cover components in said closed position surround said cutting edge on said operative portion of said surgical blade and prevent contact between said cutting edge and an operator of said article.

14. The article defined in claim 13, wherein said cover components engage one another with an interference fit in said closed position.

15. The article defined in claim 13, wherein said cover components are connected to one another by an integral hinge and said cover components are moveable with respect to one another about said hinge between said open position and said closed position.

16. The article defined in claim 13, wherein a protrusion formed on one of said cover components is positioned to mate with a recess defined in another one of said cover components when said cover components are in said closed position.

17. The article defined in claim 16, wherein said protrusion is a lengthwise ridge and said recess is a lengthwise channel.

18. The article defined in claim 16, wherein said protrusion is a stud and said recess is a hole.

* * * * *